US 8,244,483 B2

(12) United States Patent
Ballester

(10) Patent No.: US 8,244,483 B2
(45) Date of Patent: Aug. 14, 2012

(54) SHAPE RECOGNITION METHODS AND SYSTEMS FOR SEARCHING MOLECULAR DATABASES

(75) Inventor: Pedro J. Ballester, Oxford (GB)

(73) Assignee: Isis Innovation Ltd., Oxford (GB)

( * ) Notice: Subject to any disclaimer, the term of this patent is extended or adjusted under 35 U.S.C. 154(b) by 999 days.

(21) Appl. No.: 12/127,559

(22) Filed: May 27, 2008

(65) Prior Publication Data
US 2009/0006395 A1    Jan. 1, 2009

Related U.S. Application Data

(60) Provisional application No. 60/940,086, filed on May 25, 2007.

(51) Int. Cl.
*G01N 33/48* (2006.01)
*G01N 31/00* (2006.01)

(52) U.S. Cl. ............................................ 702/27; 702/19
(58) Field of Classification Search ........................ None
See application file for complete search history.

(56) References Cited

OTHER PUBLICATIONS

Silverman et al. J. Med. Chem. 1996, 39, 2129-2140.*
Ballester P. and W.G. Richards. Proc. R. Soc. A, 463, 1307-1321, Feb. 2007.*
Zyrianov J. Chem. Inf. Model. 2005, 45, 657-672.*

* cited by examiner

*Primary Examiner* — Michael Borin
(74) *Attorney, Agent, or Firm* — Thomas, Kayden, Horstemeyer & Risley, LLP

(57) ABSTRACT

The present disclosure presents novel shape comparison methods. Methods for determining shape similarity between a query molecule and a target molecule and methods for screening one or more molecules in a database based on shape similarity to a query molecule are described.

18 Claims, 10 Drawing Sheets

SHAPE RECOGNITION METHODS AND SYSTEMS FOR SEARCHING MOLECULAR DATABASES

CROSS-REFERENCE TO RELATED APPLICATION

This application claims the benefit of and priority to U.S. Provisional Patent Application No. 60/940,086, filed May 25, 2007, which is incorporated by reference in its entirety as if fully set forth herein.

BACKGROUND

Molecular databases are routinely screened for compounds that most closely resemble a molecule of known biological activity to provide novel drug leads. It is widely believed that 3D molecular shape is the most discriminating pattern for biological activity, as it is directly related to the steep repulsive part of the interaction potential between the drug-like molecule and its macromolecular target. However, efficient comparison of molecular shape is currently a challenge.

Virtual Screening is a key technique in computational drug discovery, aimed at identifying those drug-like molecules that are likely to have beneficial biological properties. It is an obvious way to reduce expensive biological tests and tackle the high failure rate currently faced by the pharmaceutical industry. In Molecular Docking, for instance, the process of docking the screened molecule to a macromolecular biological target (almost always a protein) is simulated to provide an estimate of its binding energy and thus its likelihood of being bioactive. These techniques have spurred the generation of massive databases of drug-like molecules.

An alternative Virtual Screening technique consists of searching a molecular database for compounds that most closely resemble a given query molecule. This chemical template can be a known product or inhibitor of a target protein; a natural product; or even a patented compound. The underlying assumption is that molecules similar to the active query molecule are likely to share similar properties. This similarity can be in terms of molecular shape or a range of molecular descriptors, most of which are in one way or another related to the geometry of the molecule.

Methods for molecular shape comparison can be roughly divided into two categories: superposition-based methods and descriptor-based methods. Superposition methods rely on finding an optimal super-position of molecules being compared, and descriptor-based methods (non-superposition methods) are independent of molecular orientation and position. Superposition methods are regarded as particularly effective, but not as efficient, while descriptor-based methods have higher efficiency but are generally considered to be less effective than the superposition methods.

A widely used, commercially available superposition method is ROCS (rapid overlay of chemical structures) (Rush et al., A Shape-Based 3-D Scaffold Hopping Method and Its Application to a Bacterial Protein-Protein Interaction. *J. Med. Chem.* 48, 1489-1495 (2005) which is hereby incorporated by reference herein). ROCS calculates a similarity score from the volume overlap of the molecules being compared. The required alignment is carried out through what is essentially a local optimization process, where each of the iterations involves the calculation of the volume overlap for the currently tested relative orientation and position of the molecules. Although ROCS has been touted as much more efficient than a typical superposition method, unlike other superposition methods, the same radius value is given to all heavy atoms in the molecule, which can introduce error. Furthermore, by only keeping the zero order Gaussians, ROCS calculates just the first term of the molecular volume expansion as opposed to up to the sixth term as done in an earlier superposition method (Grant et al., J. Phys Chem, 1995, 99, 3503). This introduces an error of about 75% with respect to the original method when tested on macromolecules (the magnitude of these errors on drug-sized molecules is to date undetermined).

More importantly, ROCS does not guarantee that the best superposition between the compared molecules will be found. This can be alleviated by increasing the number of starting points at the cost of further optimizations (one per starting point), thus lowering ROCS efficiency. In addition, reduced effectiveness due to suboptimal molecular overlap is very hard to detect because only the top ranked molecules are visible in practice. Those molecules that have a sufficiently similar shape to that of the query, but obtain a suboptimal molecular overlap because of superposition errors, will unnoticeably drop below the threshold and be lost among possibly millions of other rejected molecules.

Descriptor-based comparison methods use geometrical descriptors to encode the shape of molecule, with the similarity score between molecules calculated by comparing the corresponding descriptors. In one descriptor-based technique, Shape Signatures (Zauhar et al. Shape Signatures, a New Approach to Computer-Aided Ligand- and Receptor-Based Drug Design. *J. Med. Chem.* 46, 5674-5690 (2003), hereby incorporated by reference herein), each molecule is described by a histogram of the information derived from the simulation of a ray-trace reflecting within the molecular volume. Although the ranking provided by this method is largely consistent with human-perceived shape similarity, the query molecule is not ranked first in most cases, leading to questions of accuracy. While this method is quite efficient, calculating the shape signature of each molecule in the database is a very expensive procedure, which takes about 1,600 hours for a database of just 113,331 molecules on a single 450 MHz Pentium III processor.

Another descriptor-based technique is EigenSpectrum Shape Fingerprints (ESshape3D), which is a commercially available technique included in the Molecular Operating Environment (MOE 2006) software suite (MOE 2006.08 Release (http://www.chemcomp.com/)). This method starts by calculating a matrix with the Euclidean distances between all heavy atoms in the molecule to thereafter form a spectrum characteristic of its shape with the matrix's eigen values. Next, this spectrum is encoded as a fingerprint, and the similarity score is calculated as the inverse of the distance between the corresponding fingerprints. However, this method may still suffer from lower accuracy than a number of competing methods.

While more traditional descriptor based methods can be fast (in the range or 500-2000 comparisons per second on a 1995 PC), they are known to be less effective than the superposition methods and are primarily used for database pre-screening instead of stand-alone molecular shape comparison. In contrast, superposition methods can have higher accuracy rates, but comparison rates are much slower and require the previous alignment of the molecules, which is a source of errors, particularly with symmetrical query molecules. In the light of the foregoing, it is clear that none of the current shape comparison methods is completely effective.

SUMMARY

Briefly described, embodiments of this disclosure include methods for determining shape similarity to a query molecule and methods for screening one or more molecules in a database based on shape similarity to a query molecule.

One exemplary method for determining shape similarity to a query molecule, among others, includes: first, calculating a distance (d) from each atom in a molecule and a set number (n) of reference locations (RLs) in the molecule to obtain a distribution of atomic distances from each reference location (RL) of the molecule for the query molecule and for at least one target molecule; second, calculating a set number (x) of moments for each distribution of atomic distances from each RL to obtain a set number (y) of shape descriptors for the query molecule and the at least one target molecule; and third, calculating a similarity score for the query and the at least one target molecule from the set shape descriptors of the query molecule and the at least one target molecule. The resultant similarity score indicates the amount of similarity between the query molecule and the at least one target molecule. Molecules may then be ranked according to similarity scores.

Another exemplary method of the present disclosure includes screening molecules in a database based on shape similarity to a query molecule. An embodiment of this method, among others, includes: first, calculating the distance from each atom in a given molecule and a set number of RLs to obtain a distribution of atomic distances from each RL for the query molecule and for each molecule selected from the database to be searched; second, calculating a set number (x) of moments for each distribution of atomic distances from each RL to obtain a set of number (y) of shape descriptors for the query molecule and for each molecule selected from the database; and third, calculating a similarity score for the query molecule and each molecule selected from the database based on the previously calculated set of shape descriptors. The resultant similarity score indicates the amount of similarity between the query molecule (q) and a given molecule (i) selected from the database. The molecules selected from the database may then be ranked according to similarity scores.

Now having described the embodiments of the present disclosure, in general, the details of some exemplary embodiments of the methods and systems of the present disclosure are set forth in the description below. While embodiments of the present disclosure are described in connection with the description below and the corresponding figures and examples, there is no intent to limit embodiments of the present disclosure to these descriptions. Other features, objects, and advantages of the disclosure will be apparent to one of skill in the art upon examination of the following description, drawings, examples and claims. It is intended that all such additional systems, methods, features, and advantages be included within this description, be within the scope of the present disclosure, and be protected by the accompanying claims.

BRIEF DESCRIPTION OF THE DRAWINGS

The disclosure can be better understood with reference to the following drawings. The components in the drawings are not necessarily to scale, emphasis instead being placed upon clearly illustrating the principles of the present disclosure.

DETAILED DESCRIPTION

Figure 1:
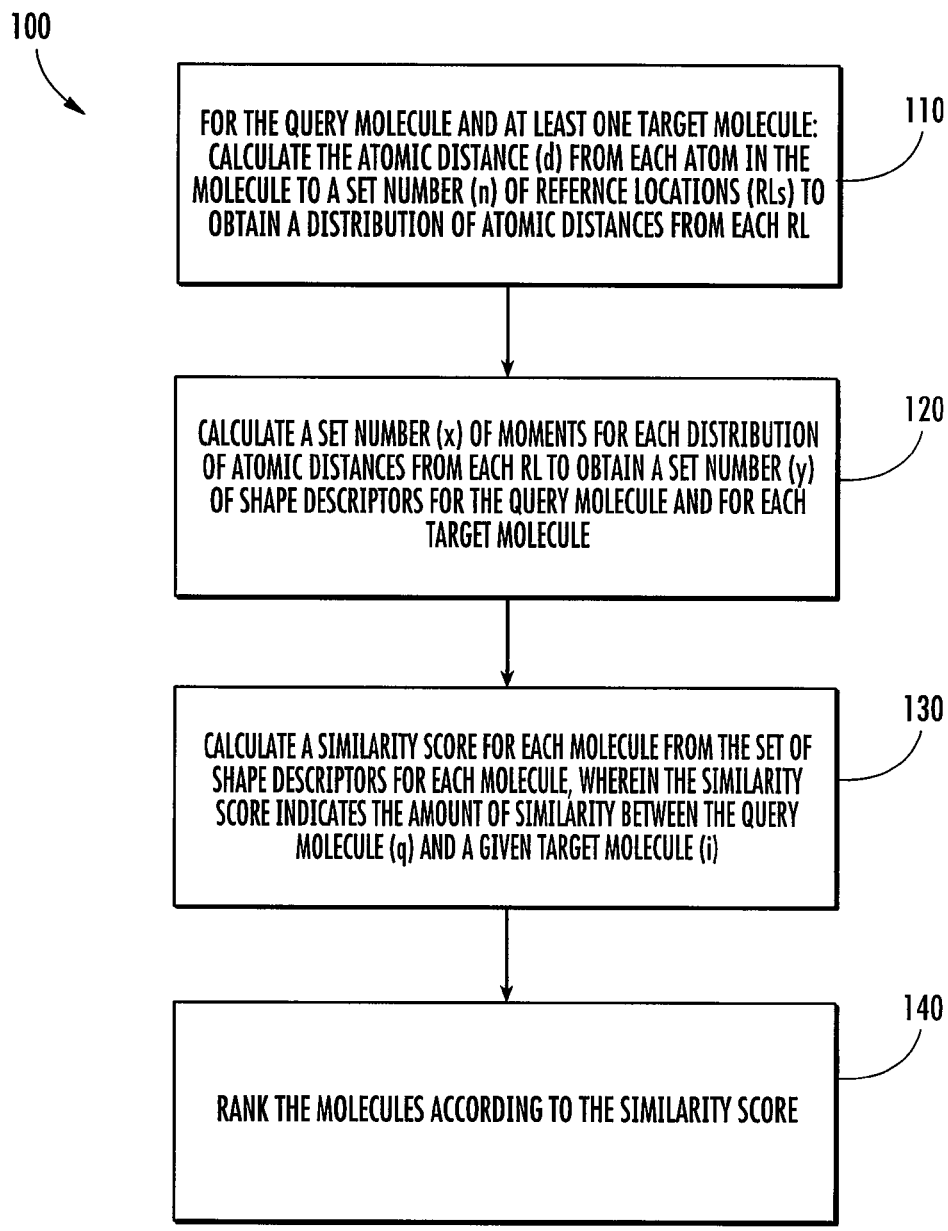
FIG. 1 is a flow chart illustrating a method according to the present disclosure for determining the shape similarity of at least one target molecule to a query molecule.

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting, since the scope of the present disclosure will be limited only by the appended claims.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

It must be noted that, as used in the specification and the appended claims, the singular forms "a," "an," and "the" include plural referents unless the context clearly dictates otherwise. Thus, for example, reference to "a support" includes a plurality of supports. In this specification and in the claims that follow, reference will be made to a number of terms that shall be defined to have the following meanings unless a contrary intention is apparent.

Discussion

The present disclosure describes methods and systems for performing methods of comparing molecules and/or screening databases of three-dimensional (3D) molecular structures based on shape recognition. The method of the present disclosure is sometimes referred to herein as Ultrafast Shape Recognition (USR). The methods of the present disclosure regard the molecule as a system of bound particles (the atoms), instead of as a solid body, as in conventional methods of shape comparison. USR is based on the observation that the shape of a molecule is uniquely determined by the relative position of its atoms. The relative position of the atoms in the molecule is in turn completely determined by a set of inter-atomic distances in the molecule (see FIG. 2). However, the complete set of all interatomic distances may contain more information than necessary to accurately describe the shape of the molecule. Thus, the methods of the present disclosure also establish a balance between the effectiveness of the method and the efficiency by varying the amount of information related to atomic distances within the molecule that is used in achieving an accurate shape description.

Indeed, only a limited number of distance values are possible between two bound atoms, which depend on the type of atoms forming the bond. In the case of distances between atoms not linked by a bond, the molecule is more flexible and more values become possible, although there will still be strong restrictions in these distance values due to intermolecular repulsion and attraction forces as well as the bonding arrangement of the molecule. In the methods of the present disclosure, a suitable subset of inter-atomic distances are chosen in order to accurately describe molecular shape while significantly reducing the associated computational cost. In particular, this subset can be chosen as the set of all atomic distances from a reduced number of strategic reference locations (RLs), which are uniquely defined in every molecule. As choosing very close molecular locations for the RLs would result in very similar sets of distances and thus essentially the same information, these locations should preferably be selected to be as separated among them as possible so as to provide the most discriminating power. While any number of RLs may be chosen, from as little as 1 to as many as all atoms in the molecule, too few RLs may not provide sufficient information to accurately describe the shape of the molecule. In turn, selecting a high number of RLs increases accuracy, but may sacrifice efficiency of the calculation.

Figure 2:
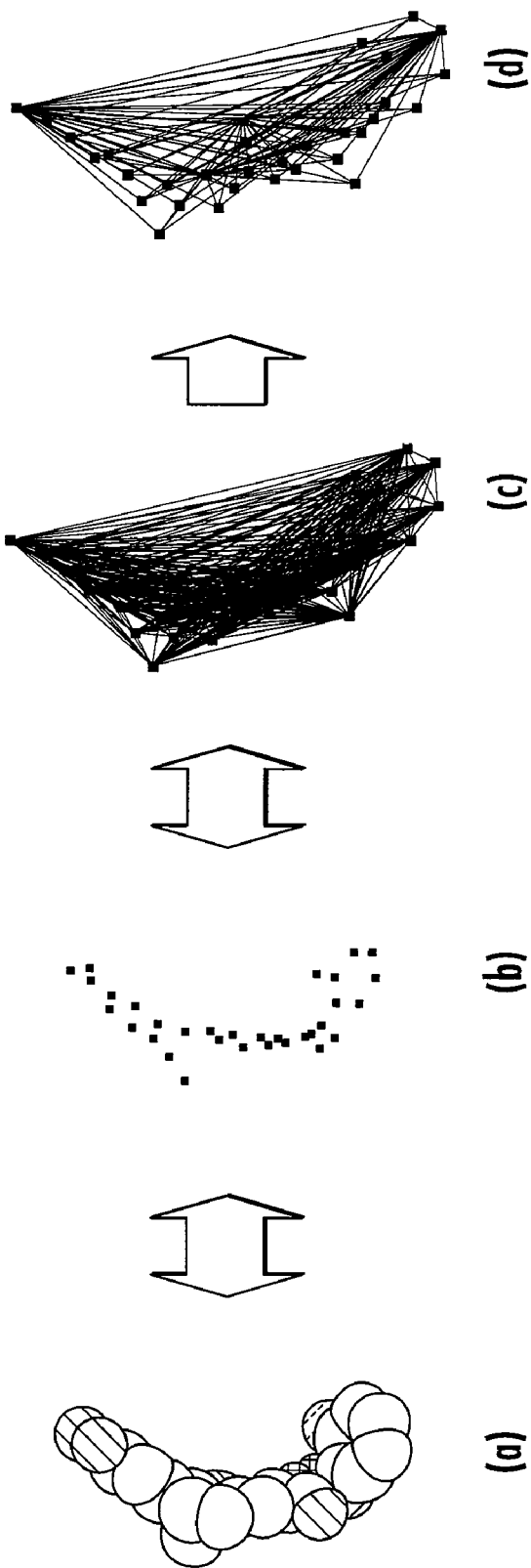
FIGS. 2 a-d illustrate four representations of molecular shape. From left to right: (a) CPK representation; (b) the set of all atomic locations; (c) the set of all inter-atomic distances; and (d) the set of all atomic distances from four reference locations (RLs).

In exemplary embodiments of the disclosure, 3 RLs can be used. In other exemplary embodiments, a set of atomic distances from four molecular reference locations (RLs) are considered. The four exemplary reference locations can be the molecular centroid (ctd), the closest atom to ctd (cst), the farthest atom to ctd (fct), and the farthest atom from fct (ftf). These locations represent the center of the molecule and its extremes, and thus are well separated. FIG. 2 provides an example illustrating these molecular shape representations. In FIG. 2 four closely related representations of molecular shape are illustrated. From left to right: (a) CPK representation, (b) the set of all atomic locations, (c) the set of all inter-atomic distances, and (d) the set of all atomic distances from the four reference locations (RLs). The CPK representation is good for visualizing the shape of a molecule. This is not necessarily the case for the set of all atomic locations and the set of all interatomic distances, although both representations contain information regarding molecular shape. Due to the inherent constraints on the values of interatomic distances, the set of all atomic distances from the four reference locations also contains sufficient information for accurately characterizing shape.

The use of a set of atomic distances from the RLs directly eliminates any need for alignment or translation, as these distributions are completely independent of molecular orientation or position. Another advantage of the present method is that, unlike superposition methods (such as ROCS), the shape information for each molecule is independently encoded. This speeds up the screening process as cross-calculations between the query and the considered molecule, which typically arise in superposition methods, are avoided.

An exemplary method of the present disclosure is briefly described in the flowchart 100 of FIG. 1. First, a set number (n) of RLs in a given molecule is chosen. Then, as shown in step 110 of FIG. 1, the atomic distance (d) from each atom (or a selected subset of atoms) in the molecule to each RL is determined. This provides a distribution of atomic distances from each RL for each molecule of interest: namely, the query molecule and one or more target molecules (e.g., a single target molecule or a plurality of molecules selected from a database to be screened). The resulting set of distributions of atomic distances is then used to calculate molecular descriptors for each molecule (step 120) which are used to determine a similarity score (step 130). The shape comparison methods of the present disclosure can be used to compare a query molecule to a single target molecule (e.g., the comparison molecule), a select number of target molecules, or an entire database of target molecules.

To calculate the atomic distances (d), first, the three dimensional position vector for each atom is read. Thereafter, the locations of each RL to be used of the molecule is determined from the atomic positions. For instance, if one of the RLs to be used is the molecular center ((centroid), (ctd)), then the atomic location of ctd is determined. Next, a set of Euclidean distances of all atoms to the molecular centroid is calculated. In some embodiments, a subset of atoms is used (e.g., all atoms in a molecule except the hydrogens), and thus the distances from each atom of the selected subset to the RL is calculated. These are regarded as samples from the distribution of all atomic distances from the molecular centroid ($d^{ctd}$):

$$\{d_j^{ctd}\}_{j=1}^N \text{ where } N \text{ is the number of atoms of the considered molecule} \quad (1)$$

This process is repeated for each of the set number (n) of RLs to be used.

In the methods of the disclosure the molecular shape of a molecule may be characterized through a set of 1D distributions, which retains 3D shape information since such a dimensionality reduction can significantly improve the efficiency of the method. At this stage, each molecule is described by as many features (the 1D distribution of atomic distances) as number of atoms in the molecule. This raises the obvious question of how to compare molecules with different number of atoms. That difficulty is circumvented by defining a fixed number of moments of the 1D distributions, whose values characterize the molecule considered. Thus the next step 120, as illustrated in FIG. 1, is to calculate a set number (x) of moments for each distribution of atomic distances from each RL to obtain a set number (y) of shape descriptors for the query molecule and for each target molecule.

The first moments of each of the set of distributions of atomic distances are calculated in order to characterize the geometry of the molecule and thus its shape. Such approach can be based on a theorem from statistics which proves that a distribution is completely determined by its moments. (Hall, P. Z. Wahrscheinlichkeitstheorie verw. Gebiete 1983, 62, 355, which is hereby incorporated by reference herein.) While any number of moments may be used in the methods of the present disclosure, as with the number of RLs, there is a balance between accuracy and efficiency that correlates to the number of moments used in the calculation. In an exemplary method of the present disclosure, the first three moments of each distribution were chosen, because they provide a compromise between the efficiency and effectiveness of the method. The first three moments will be described below with respect to the RL ctd, but it will be understood by one of skill in the art that the same moments can be calculated for any RL.

Figure 3:
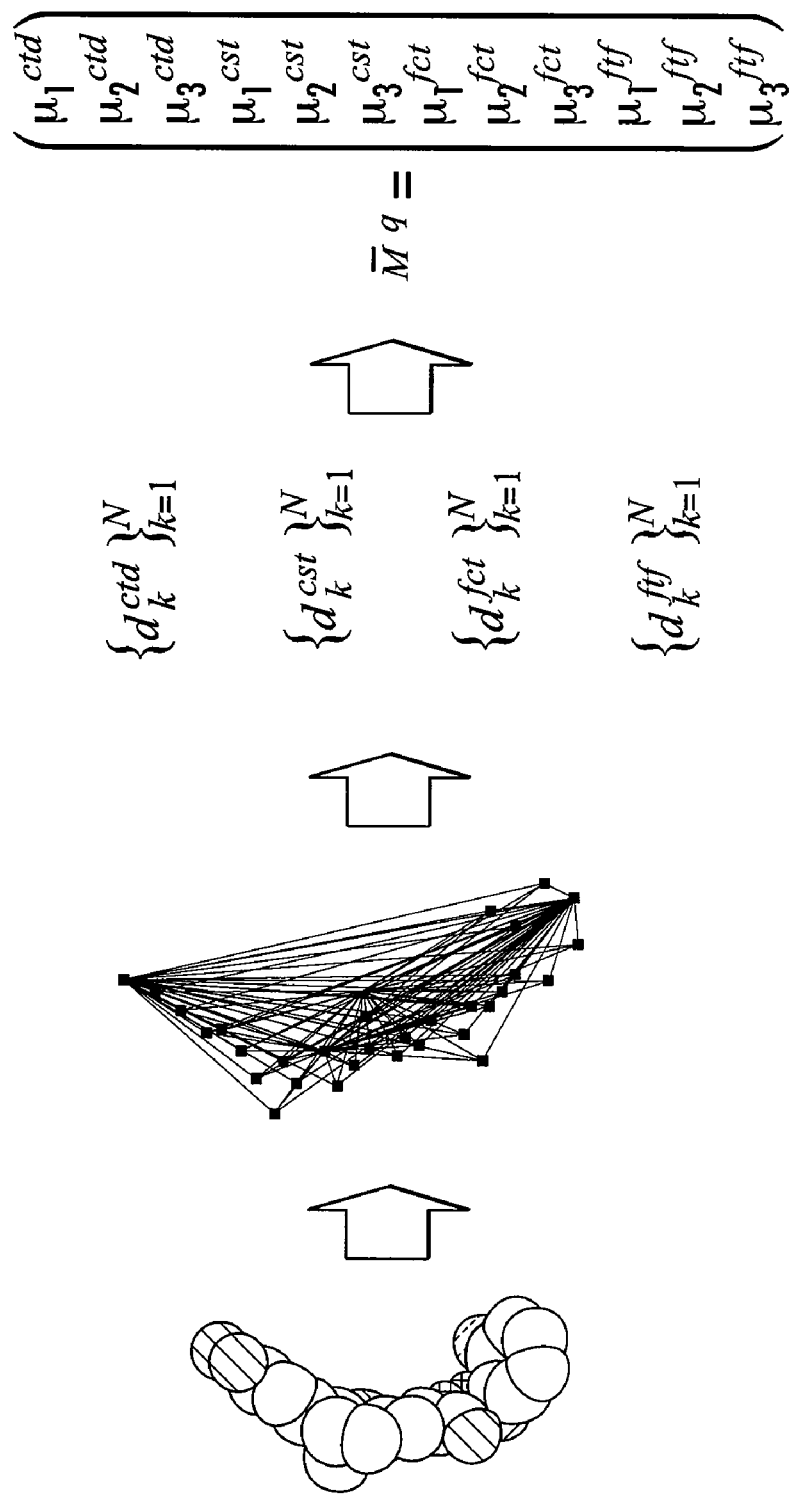
FIG. 3 illustrates a vector of 12 geometric shape descriptors for a selected molecule, determined according to a method of the present disclosure.

The first moment ($\mu_1^{ctd}$) corresponds to the first moment of the distribution of atomic distances from the molecular centroid. This represents the average atomic distance to the molecular centroid, and thus it provides an estimate of the molecular size. The second moment ($\mu_2^{ctd}$) is the variance of these atomic distances about $\mu_1^{ctd}$ (i.e., a measure of the compactness of the molecule). The third moment ($\mu_3^{ctd}$) is the skewness of these atomic distances about $\mu_1^{ctd}$ (i.e., a measure of the asymmetry of the distribution). To calculate full set of shape descriptors, the process is repeated for every RL for each molecule to be considered. In an embodiment where the 4 RLs described above are used (ctd, cst, fct, and ftf), calculation of the first three moments for each RL gives a total of 12 shape descriptors for each molecule. Thus, in the embodiment described above, the moments for the three remaining distributions: $\{d_j^{cst}\}_{j=1}^N$, $\{d_j^{fct}\}_{j=1}^N$ and $\{d_j^{ftf}\}_{j=1}^N$, are calculated, where the superscript indicates the RL. Of course, as mentioned previously, one can include more reference locations leading to more descriptors and thus an even more accurate description of shape. In the exemplary embodiment described above and shown in the flowchart of FIG. 6, the first three moments from each of four considered 1D distributions are used to describe a molecule $$\vec{M}=(\mu_1^{ctd},\mu_2^{ctd},\mu_3^{ctd},\mu_1^{cst},\mu_2^{cst},\mu_3^{cst},\mu_1^{fct},\mu_2^{fct},\mu_3^{fct},\mu_1^{ftf},\mu_2^{ftf},\mu_3^{ftf}),$$

since this choice provides a compromise between the efficiency and the effectiveness of the method of the present disclosure. The use of moments to achieve 12 molecular shape descriptors is illustrated for an exemplary molecule in FIG. 3. In FIG. 3, each molecule has associated a unique vector of geometrical descriptors, which spans a 12-dimensional molecular shape space. These descriptors are statistical moments of the set of all atomic distances from the four selected strategic reference locations (RLs).

While different methods can be devised by one of skill in the art for calculating the moments of atomic distributions, an exemplary calculation of the first three moments is described as follows. The $l^{th}$ moment about the origin ($m_l$) is the expectation of the $l^{th}$ power of d and thus is defined as:

$$m_l = E[d^l] = \sum_{j=1}^N w_j d_j^l \quad (2)$$

As every atom is considered to contribute equally to the molecular shape, the weights are set to the same value $w_j=1/N$ and thus equation (2) becomes:

$$m_l = \frac{1}{N}\sum_{j=1}^N d_j^l \quad (3)$$

These are the molecular moments about the origin. In order to obtain molecular descriptors with improved interpretability of molecular geometry, the definition of moments about the mean ($\mu_l$) is invoked:

$$\mu_l = E[(d-m_1)^l] \quad (4)$$

By developing this expression using equations (2) and (3), the final equation for calculating the $l^{th}$ molecular moments about the mean (called simply moments henceforth) is obtained:

$$\mu_l = \sum_{n=0}^l \binom{l}{n}(-1)^n m_1^n m_{l-n} \quad (5)$$

The first three moments are therefore:

$$\mu_1=0$$

$$\mu_2=m_2-m_1^2$$

$$\mu_3=m_3-3m_1m_2-2m_1^3$$

Note that the first moment $\mu_1$ gives no information and hence is substituted by the first moment about the origin $m_1$ (for the generic expression of the moments about the origin see equation 3). As noted above, the first three moments were chosen because these moments can be easily related to geometrical properties of the molecule. For instance, $m_1$ is the average atomic distance to the molecular centroid and hence it gives an idea of the size of the molecule. Analogue interpretations can be drawn from $\mu_2$ (variance) and $\mu_3$ (skewness).

As mentioned above and illustrated by the flow chart in FIG. 6, this procedure is repeated for each of the selected RLs (e.g., the four reference points, denoted by the superscripts ctd, cst, fct and ftf), so that every molecule is described by a set of descriptors. In the exemplary example used herein, a set of 12 descriptors is obtained. In a further embodiment, the same dimensionality is given to each descriptor. This reduces imbalances between the terms (e.g., higher moments shadowing the contribution of lower moments) in equation 6, below. For instance, the variance $\mu_2$ becomes the standard deviation $(\mu_2)^{1/2}$, which has the same distance units as the first moment (usually Amstrongs). This is illustrated below.

$$\vec{M} = \begin{pmatrix} m_1^{ctd}, (\mu_2^{ctd})^{\frac{1}{2}}, (\mu_3^{ctd})^{\frac{1}{3}}, m_1^{cst}, (\mu_2^{cst})^{\frac{1}{2}}, (\mu_3^{cst})^{\frac{1}{3}}, \\ m_1^{fct}, (\mu_2^{fct})^{\frac{1}{2}}, (\mu_3^{fct})^{\frac{1}{3}}, m_1^{ftf}, (\mu_2^{ftf})^{\frac{1}{2}}, (\mu_3^{ftf})^{\frac{1}{3}} \end{pmatrix}$$

In yet other embodiments, different weight may be given to one or more of the moments used. In other words, greater importance may be assigned to one moment representing a particular trait of a molecule (e.g., size, compactness, etc.).

Figure 6:
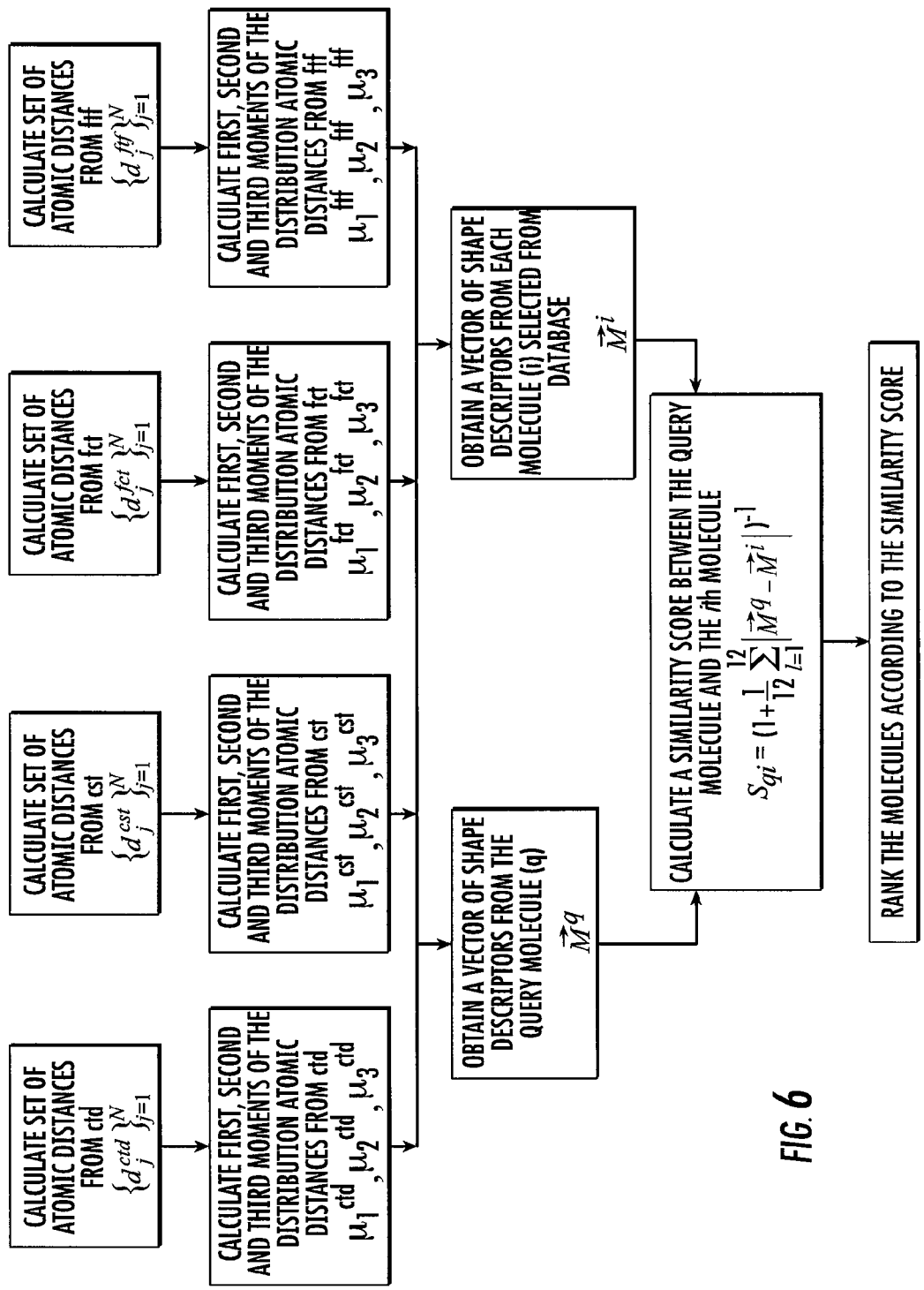
FIG. 6 is a flow chart illustrating an embodiment of a method according to the present disclosure for screening molecules selected from a database for shape similarity to a query molecule.
Figure 7A:
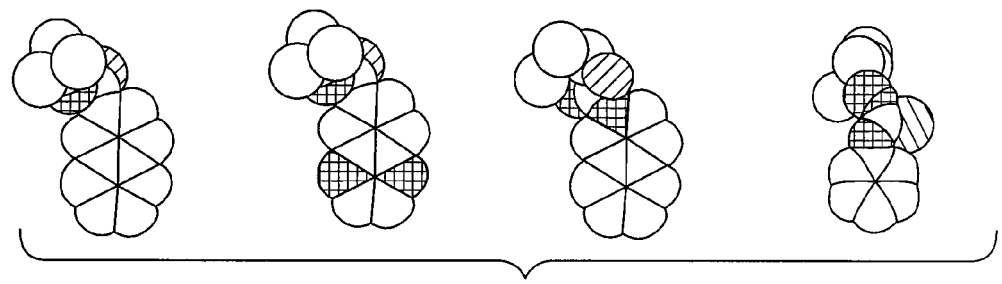
FIG. 7 illustrates the top ranked target molecules for 5 different query molecules (a-e) in a database of 2,433,493 compounds screened using a method of the present disclosure. In each case the query molecule is the highest ranked molecule (far left in each row), with a similarity score of 1.
Figure 7B:
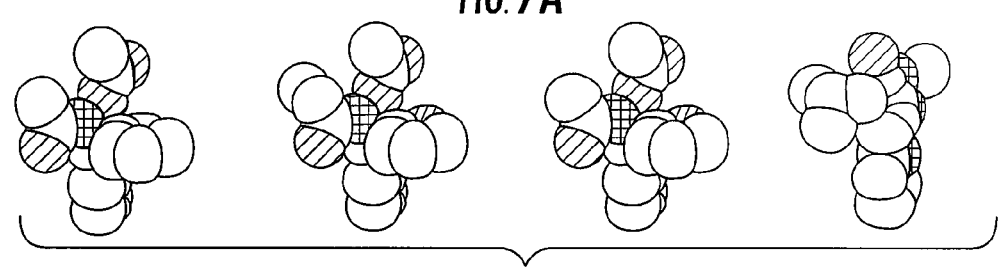
Figure 7C:
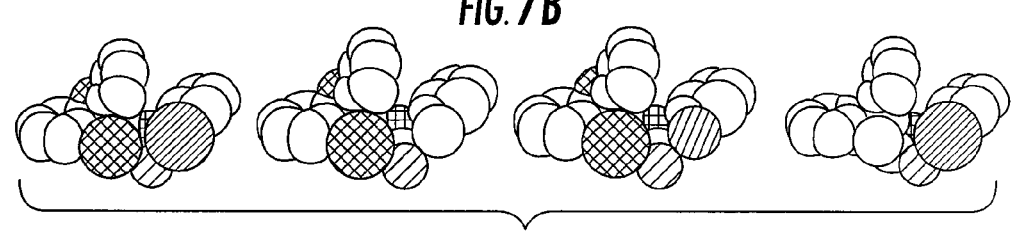
Figure 7D:
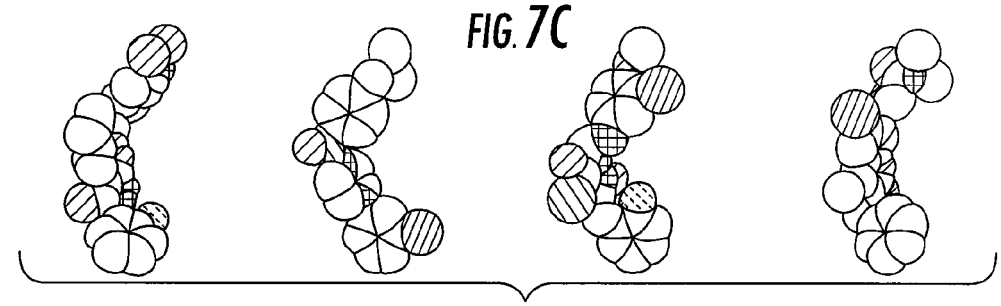
Figure 7E:
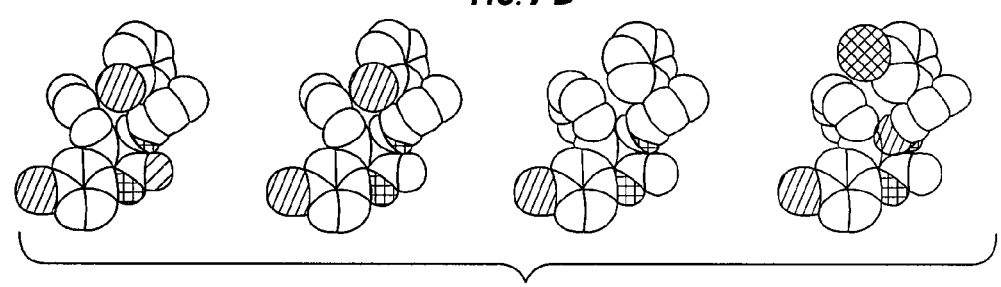
Figure 8A:
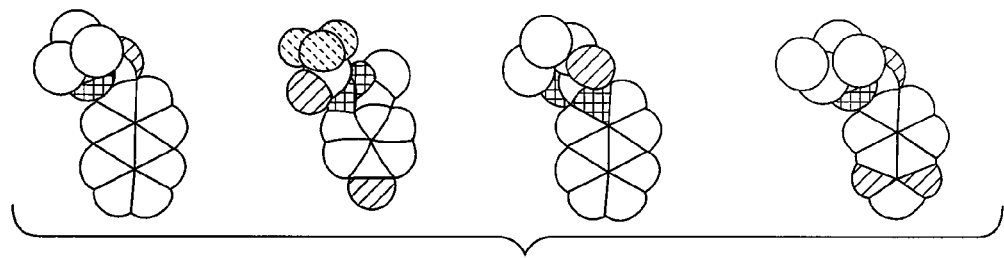
FIG. 8 illustrates the top ranked target molecules for the same 5 query molecules from FIG. 7 (a-e) in a database of 2,433,493 compounds screened using the ESshape3D method.
Figure 8B:
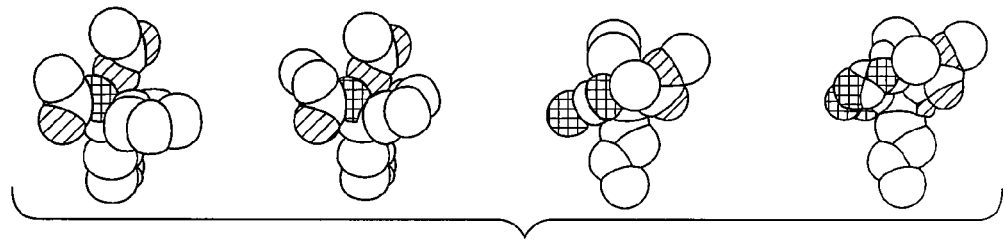
Figure 8C:
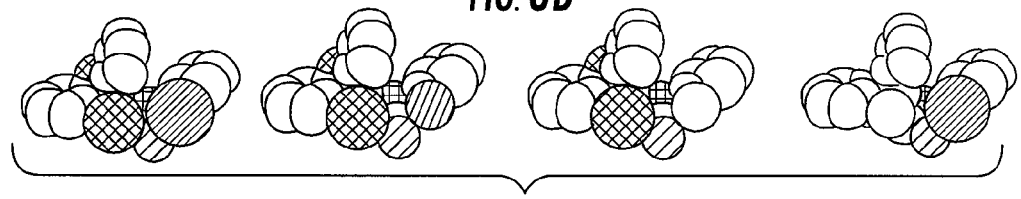
Figure 8D:
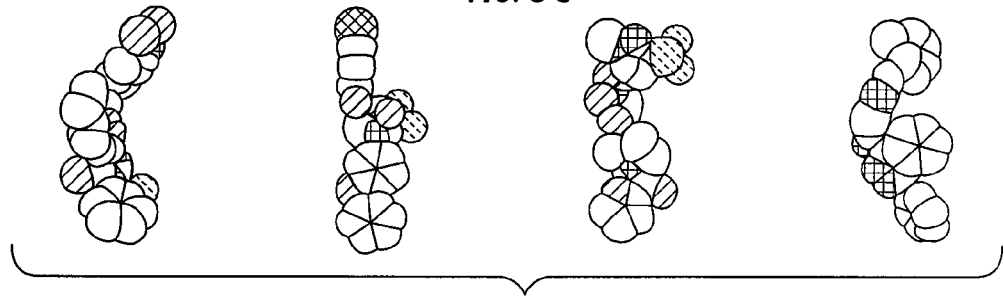
Figure 8E:
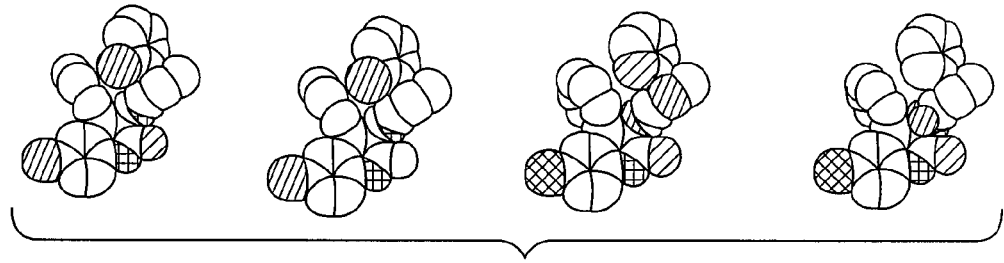

As illustrated in FIG. 1, after determination of the set of shape descriptors for each molecule from the calculation of the moments (120), a similarity score is calculated (130) for the query molecule (q) and at least one target molecule (i). If more than one target molecule is being compared to the query molecule, for example a database of molecules, then the molecules in the database can be ranked (140) according to their respective similarity scores to the query molecule. FIG. 6 illustrates a flow chart of a representative example of screening a database of molecules for shape similarity to a query molecule (q) by calculating similarity scores for the query molecule and each molecule (i) in a database and ranking the molecules according to the similarity score.

The similarity score can be calculated according to any one or more of a number of methods. For example, a normalised score function can be used to quantify the degree of similarity (a similarity score) between molecules based on the shape descriptors. Any monotonic inverse function of the distance between the molecules in descriptor space can be used to provide the normalised similarity score. Either the Manhattan distance or the Euclidean distance, or any other distances can be used.

Figure 4:
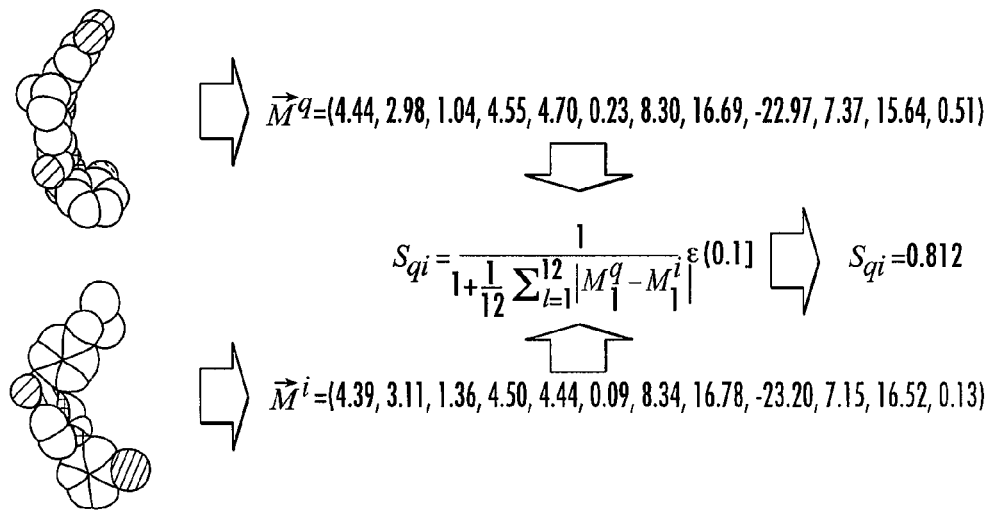
FIG. 4 illustrates an exemplary calculation of a similarity score for a selected query molecule and a target molecule.
Figure 5:
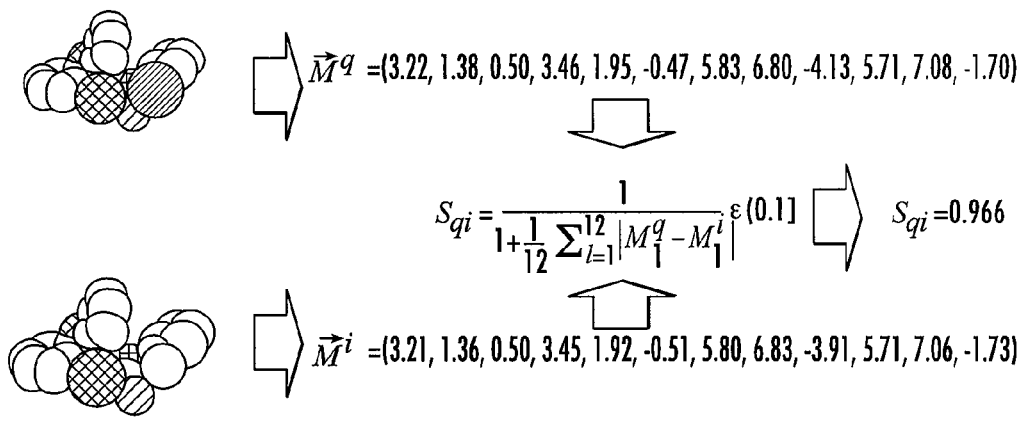
FIG. 5 illustrates an exemplary calculation of a similarity score for a second selected query molecule and a target molecule.

In an exemplary embodiment, the following calculation is used to determine similarity score. First, the Manhattan distance between the vectors of shape descriptors of the query and the currently screened molecule is calculated and divided by the number of descriptors. The resulting dissimilarity measure is transformed into a normalised similarity score by translating the dissimilarity by one unit and inverting the resulting value. The similarity score function $S_{qi}$ is therefore:

$$S_{qi} = \left(1 + \frac{1}{12}\sum_{l=1}^{12}|M_l^q - M_l^i|\right)^{-1} \quad (6)$$

Where $0 \leq S_{qi} \leq 1$ and $\vec{M}^q$ and $\vec{M}^i$ are the vectors of shape descriptors for the query and $i^{th}$ screened molecule, respectively. A $S_{qi}$ value of 1 indicates maximum similarity between the query molecule and a target molecule, and a value of 0 indicates minimum similarity. Examples of the calculation of similarity scores for two query molecules and target molecules from a database are illustrated in FIGS. 4 and 5. As mentioned above, other ways to define a normalised similarity score could be of course adopted, as long as the similarity score is inverse-monotonic with respect to the dissimilarity, so as to preserve the ranking order.

The accuracy with which the present USR method describes molecular shape and thus its effectiveness as a molecular shape comparison method is shown in the examples below. The following representative comparisons also highlight some interesting features of the present method. The first example illustrated in FIG. 4 shows that molecules with similar shape, but different number of atoms, can be found with USR. The top molecule has 33 heavy atoms compared to the 26 heavy atoms which forms the molecule at the bottom. Despite being calculated with a significantly different number of atomic distances, both vectors of shape descriptors are quite similar because the relative positions of the atoms in both molecules are quite similar as well. USR assigns a high score, S=0.812, to these similarly shaped molecules.

The second example, in FIG. 5 gives an idea of the high discriminating power provided by USR. Both molecules in FIG. 5 differ only in one atom, which in turn introduces a slight difference in the corresponding distance distributions and ultimately in the calculated shape descriptors. Each descriptor has a very similar, but still different value for each molecule, although it is not always appreciable from the values reported in FIG. 5 due to the truncation at the second decimal.

In addition to being highly effective, USR is expected to be extremely fast. One reason for such efficiency is that the defined shape descriptors only require the calculation of 4N distances along with a total of 12 moments of the resulting four distributions. Unlike USR, other shape comparison methods are based on much more expensive operations such as, for example, the calculation of molecular surface or molecular volume, which usually need to be performed for many tens of different relative superpositions as a part of an optimization process. However, a reason for the ultrafast comparison rate provided by USR is that, unlike superposition methods, the shape information of each molecule is independently encoded as a vector of shape descriptors, which is consistent with the status of shape as an intrinsic geometrical property of the molecule. This speeds up the screening process as cross-calculations between the query and the considered molecule, which typically arise in superposition methods, are avoided. As a consequence, once these shape vectors have been calculated for the whole database, comparing shapes of two molecules involves simply evaluating the corresponding similarity score, an operation that has the minimal computational cost of calculating the inverse of the distance between two vectors of shape descriptors.

Portions of the present disclosure are also described in the following publications, which are hereby incorporated by reference herein in their entireties: Ballester, Pedro J., Richards, W. Graham, Ultrafast Shape Recognition to Search Compound Databases for Similar Molecular Shapes, J Comput Chem, 2007, published online www.interscience.wiley.com; and Ballester, Pedro J., Richards, W. Graham, Ultrafast Shape Recognition for Similarity Search in Molecular Databases, Proc. R. soc. A 463, 1307-1321, 2007. These publications include the examples below and additional data supporting the present disclosure.

EXAMPLES

The following examples were performed to test the methods of the present disclosure described above. These examples were carried out with a database that contains 2,433,493 commercially available compounds. Each database entry represents the chemical structure of the compound in 3D MDL SD format (without including Hydrogen atoms). The database was generated to contain only one conformer per compound, with each of them having at least 10 heavy atoms.

The first example is intended to evaluate the efficacy of the proposed descriptors for accurately encoding shape. This was a complicated endeavour as no shape comparison method has been shown to be completely accurate at describing shape, and therefore there were no grounds for comparison. A number of studies have addressed this difficulty by visually comparing the top ranked molecules provided by the shape comparison method. FIG. 7 shows the screened molecules with the highest USR score for five different queries. Note that, given the large database size (2,433,493 molecules), a small inaccuracy in the shape description would result in dissimilar molecules within the top ranked subset, which is not observed in FIG. 7. For each row (a-e), the four highest ranked molecules out of the 2,433,493 compounds constituting the vendor database are presented. The query molecule (q) is the highest ranked molecule in all cases (with a Similarity Score equal to 1) and thus appears always as the first on the left in each row. This figure shows that the method succeeds in finding very similarly shaped compounds for diverse, in terms of number of atoms and types of shape, query molecules. The first query molecule (for row (a)) has 17 atoms (scores are: $S_1=1.000$, $S_2=0.976$; $S_3=0.934$, and $S_4=0.908$). The second query molecule (row (b)) has 25 atoms ($S_1=1.000$, $S_2=0.912$, $S_3=0.909$, and $S_4=0.892$). The third query molecule (row (c)) has 30 atoms ($S_1=1.000$, $S_2=0.966$, $S_3=0.960$, and $S_4=0.957$). The fourth query molecule (row (d)) has 33 atoms ($S_1=1.000$, $S_2=0.812$, $S_3=0.788$, and $S_4=0.785$). The fifth query molecule (row (e)) has 38 atoms ($S_1=1.000$, $S_2=0.971$, $S_3=0.890$, and $S_4=0.884$). These queries were selected because they represent a diverse subset of the chemical space in terms of number of atoms and type of shape, but results of similar quality were observed in every additional query made using USR. The present method is able to identify shapes that closely resemble that of the query, which is also in the database and it is the highest ranked molecule in all cases. In addition, this example shows that the method is particularly good at finding different chemical scaffolds, as it can be observed from the fourth query (d) in FIG. 7, which constitutes a very valuable capability.

An even stronger validation can be carried out by comparing these hits against those provided by another shape comparison method, in order to investigate whether USR misses any molecule with a significantly more similar shape. FIG. 8 shows the screened molecules with the highest ESshape3D score for the same queries as in FIG. 7. ESshape3D also retrieves the query molecule with a maximum similarity score in all cases and thus appears on each row (query) as the first molecule on the left. The top hits for the third and fifth queries (c, e) have a consistent ranking and are quite similar to those obtained with USR (compare with FIG. 7). However, the remaining three queries (a, b, d) have top hits which are not as similar to the query molecule as the USR top hits. This is particularly noticeable in the fourth query (d), where the second, third and fourth most similar molecules are visually much more dissimilar to the query than the corresponding USR top hits.

Figure 9A:
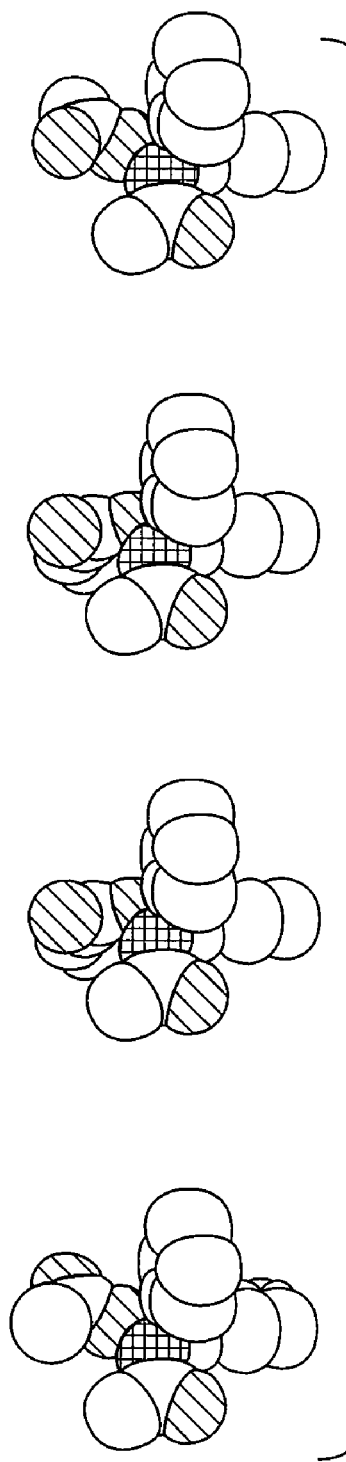
FIG. 9 illustrates the top ranked conformers (out of 292 conformations) of the second query molecule from FIG. 7 using the USR method of the present disclosure (a) and using the ESshape3D method (b).
Figure 9B:
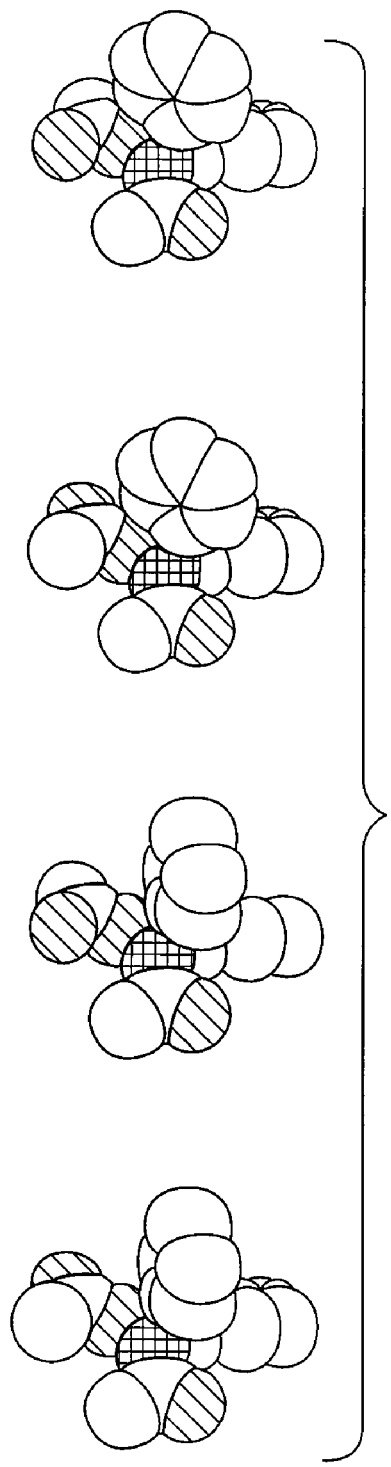

It could be argued that the procedure used to locate the reference points in USR might be sensitive to small details of the conformation rather than the overall shape of the molecule. However, similarly shaped conformers share a similar relative position of their respective atoms in the 3D space, and therefore the location of the reference points should be similar as well. In order to illustrate this issue, an additional 292 confirmations of the molecule used for the second query (b) in FIG. 7, which has four possible extremes were calculated. This is illustrated in FIG. 9. The top row shows the conformers with the highest USR scores, while the bottom row shows those conformers with the highest ESshape3D scores. Again, it is observed that USR retrieves more similarly shaped conformers than ESshape3D, despite the presence of multiple conformers of the query molecule.

Figure 10:
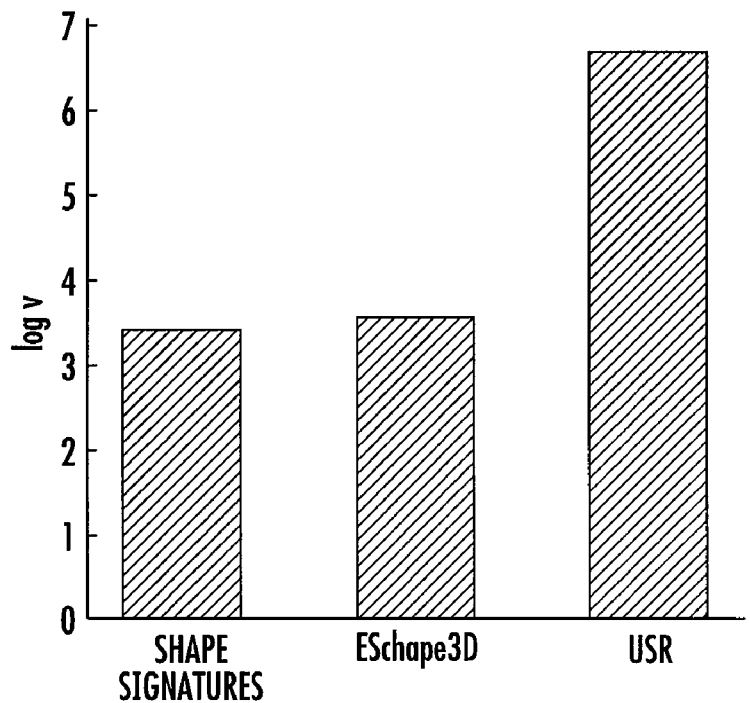
FIG. 10 is a bar graph comparing the efficiency (in logarithm of screened molecules per second) of a method of the present disclosure (USR) and two other known descriptor based shape comparison methods (ESshape3D and Shape Signatures).

Another area to investigate is the efficiency of the method. With this purpose, the molecular shape comparison rate will be calculated for USR and compared to that from three state of the art methods: ESshape3D, Shape Signatures and ROCS. Unlike ESshape3D, a direct efficiency comparison with the last two methods is not possible. However, it is still possible to make an approximate comparison because these methods were recently published and thus access is available to computers with similar power to that used in the studies where their efficiency was reported. In this way, FIG. 10 presents the comparison rate of USR versus the two descriptor-based shape methods, ESshape3D and Shape Signatures. An efficiency comparison (in logarithm of screened molecules per second) between USR and these two state-of-the-art descriptor-based shape methods is illustrated. The rate for USR and ESshape3D was calculated on a modestly powerful PC (AMD Athlon XP 1800+CPU at 1.5 GHz with 512 MB of memory), which is also very similar to that used in Shape Signatures (Zauhar et al., J. Med Chem 2003, 46, 5674). USR is 1,546 and 2,038 times faster than ESshape3D and Shape Signatures, respectively.

Figure 11:
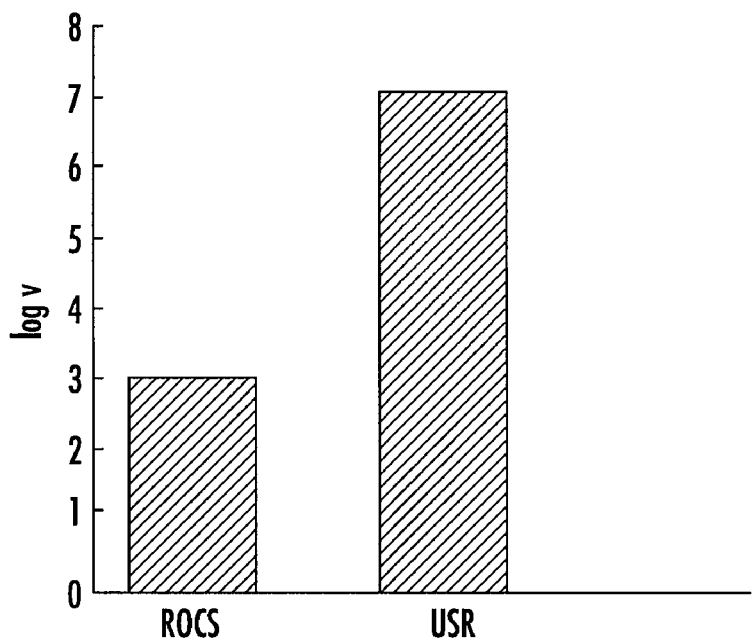
FIG. 11 is a bar graph comparing the efficiency (in logarithm of screened molecules per second) of a method of the present disclosure (USR) and a known superposition-based shape comparison method (ROCS).

In FIG. 11, an approximated comparison with the superposition-based method ROCS is made in the form of an efficiency comparison (in logarithm of screened molecules per second) between the present method (USR) and ROCS (Rush et al. 2005), a widely used superposition-based shape comparison method. As ROCS is not available for validation studies, an approximate comparison is presented based on its reported (Rush et al. 2005) comparison rate on a modern Intel/AMD processor. Therefore, USR was run on one of the cores of an Intel Core2 2.93 GHz processor with 4 GB of memory. USR obtained a comparison rate of 14,238,500 molecules per second, which is hence about 14,238 times faster than that reported by ROCS. It is worth noting that ROCS is widely regarded as the fastest superposition-based method, and it has been claimed to be order of magnitudes faster than other 3D methods.

USR efficiency makes it sufficiently fast to extract information from the largest molecular databases available, as it would be able to identify the most similar shapes out of the 3.5 billion molecules constituting the screensaver database in about 4 minutes on a single processor. To illustrate further the significance of USR, consider a possible research scenario where one would like to find the most similarly shaped compounds within the screensaver database for each query in a set of 100 interesting molecules. This would take about 7 hours with USR. By contrast, ESshape3D, Shape Signatures and ROCS would take about 1.2, 1.6 and 11.1 years, respectively. This ability to handle larger databases is considered an important component to addressing the future of the pharmaceutical industry.

The last example presents an interesting capability of USR. Unlike superposition methods, where shape can only be calculated with respect to the overlapping molecule, USR defines the shape of a molecule independently and using a fixed set of descriptors for every molecule. The latter ensures that every molecule will have a unique location in the 12-dimensional chemical space spanned by the used descriptors. This is a major advantage when finding and visualizing clusters of molecules with similar shape. There are many applications of such representation. For instance, each of these clusters is a region of the chemical space with similarly shaped molecules, and thus it could be regarded as compounds that are likely to share similar biological activity with the query molecule. In addition, such representation shows at a glance where the geometry of the compared molecules differs. In combination with a suitable clustering algorithm, one could find clusters in a molecular database in order to select the most representative molecule of each cluster. The latter could be applied, for example, as a way to avoid repeating expensive biological tests on similar molecules. Exemplary clustering algorithms include Agglomerative Hierarchical Clustering and K-means Clustering, but other suitable algorithms are known to those of skill in the art.

Figure 12:
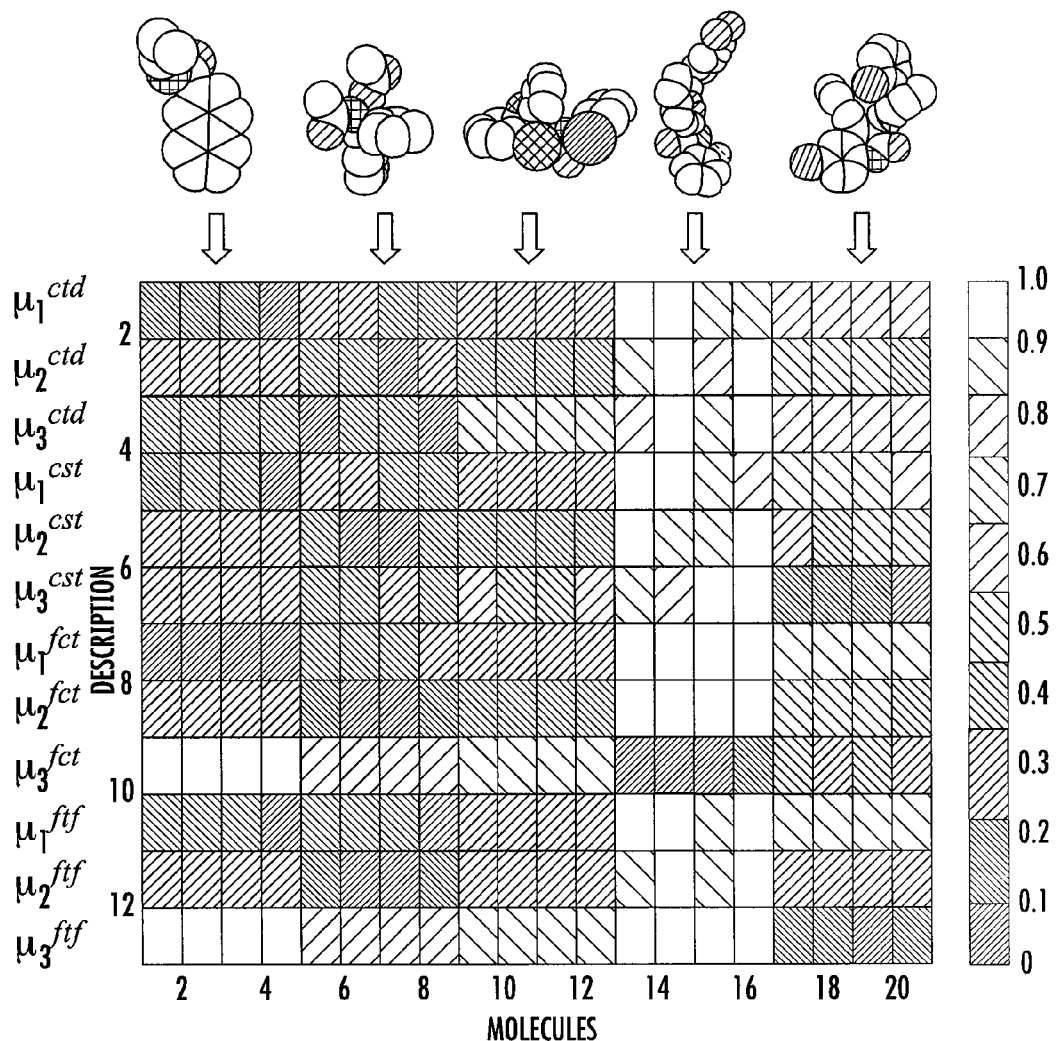
FIG. 12 illustrates a 12-dimensional representation of a region of the chemical space according to 3D shape for a set of query molecules and highest ranked target molecules for each query molecule. Each column corresponds to the molecules from FIG. 7, and each row is one of 12 molecular descriptors. The molecules are ordered in clusters where each cluster contains the four most similar molecules to the query molecule (pictured on the top).

FIG. 12 shows an example of this representation based on the results of five queries presented in FIG. 7. FIG. 12 presents a twelve-dimensional representation of a tiny region of the chemical space according to three-dimensional shape. Each column corresponds to a molecule from FIG. 7 and each row is one of the molecular descriptors whose normalized values are given by the key on the right (note that such normalization does only allow a direct comparison of molecules across a single molecular descriptor at a time). The molecules are ordered in clusters (a cluster is defined as a group of molecules which are similar among themselves, but dissimilar when compared with molecules from other clusters). Each cluster contains the four most similar molecules to the query molecule (pictured on the top).

Accordingly, a new method, referred to herein as Ultrafast Shape Recognition (USR), is provided based on moments of inter-atomic distance distributions. It was motivated by the relative inefficiency of current shape comparison methods, which are not able to cope with the largest molecular databases available in a reasonable time. USR has been shown to effectively search molecular databases at least 1,546 times faster than current methodologies. Also, the problematic requirement of aligning molecules for comparison is circumvented, as the proposed distributions are independent of the spatial orientation of database molecules. Lastly, in an exemplary embodiment, the way USR encodes shape provides every molecule with a unique location in the 12-dimensional chemical space spanned by the used shape descriptors. This opens the door to the application of existing clustering algorithms to find groups of similar molecules as a way to analyze the molecular diversity of a database in terms of molecular shape.

The method can be also adapted to tackle similar shape comparison problems in other fields, such as designing content-based Internet search engines for 3D geometrical objects (Funkhouser, T., et al. 2005 Shape-based retrieval and analysis of 3D models. Commun. ACM 48, 58-64) or performing fast similarity comparisons between macromolecules (e.g. proteins)(Albrecht, B., et al. 2004 Evaluation of structural similarity based on reduced dimensionality representations of protein structure. Protein Eng. Design Select. 17, 425-432). From a broader perspective, ultrafast pattern recognition may soon become not only useful, but essential. In most areas of modern science, the amount of archived data is increasing at an explosive rate and its analysis is becoming more and more complex, a trend that it is expected to continue in the foreseeable future. However, this data explosion has not resulted in an information explosion, mainly because of the difficulties of current methods to cope with massive databases. It is believed that the presented approach is one way to tackle the enormous challenge posed by scientific data explosion in pattern recognition in general and molecular shape comparison in particular.

It should be emphasized that the embodiments of the present disclosure, particularly any "preferred" embodiments, are merely possible examples of the implementations, merely set forth for a clear understanding of the principles of the disclosure. Many variations and modifications may be made to the above-described embodiment(s) of the disclosure without departing substantially from the spirit and principles of the disclosure. All such modifications and variations are intended to be included herein within the scope of this disclosure, and the present disclosure and protected by the following claims.

I claim:

1. A computer-implemented method for determining shape similarity to a query molecule comprising:
    calculating, using the computer, a distance (d) from each atom in a molecule and a set number (n) of reference locations (RLs) in the molecule to obtain a distribution of atomic distances from each reference location (RL) of the molecule for the query molecule and for at least one target molecule;
    calculating a set number (x) of moments, using the computer, for each obtained distribution of atomic distances from each RL to obtain a set number (y) of shape descriptors for the query molecule and the target molecule; and
    calculating a similarity score, using the computer, for the query molecule and target molecule from the set of shape descriptors for each molecule, wherein the similarity score indicates the amount of similarity between the query molecule and the at least one target molecule, wherein n is at least 3.

2. The method of claim 1, wherein n is at least 4 and wherein the reference locations comprise at least the following reference locations: the molecular centroid (ctd), the closest atom to ctd (cst), the farthest atom from ctd (fct), and the farthest atom from fct (ftf).

3. The method of claim 1 wherein x is at least 3.

4. A computer-implemented method for determining shape similarity to a query molecule comprising:
    calculating a distance (d) from each atom in a molecule and a set number (n) of reference locations (RLs) in the molecule, using the computer, to obtain a distribution of atomic distances from each reference location (RL) of the molecule for the query molecule and for at least one target molecule;
    calculating a set number (x) of moments, using the computer, for each obtained distribution of atomic distances from each RL to obtain a set number (y) of shape descriptors for the query molecule and the target molecule; and
    calculating a similarity score, using the computer, for the query molecule and target molecule from the set of shape descriptors for each molecule, wherein the similarity score indicates the amount of similarity between the query molecule and the at least one target molecule, and
    wherein the moments are selected from at least the first three moments of the distribution of atomic distances from the reference location, wherein the first moment is the mean atomic distance to the reference location, the second moment is the variance of the atomic distances from the reference location, and the third moment is skewness of the atomic distances about the reference location.

5. The method of claim 1, wherein n is 4 and x is 3, resulting in 12 shape descriptors for calculation of the similarity score.

6. A computer-implemented method for determining shape similarity to a query molecule ($\vec{M}^q$) comprising:
    calculating, using the computer, a distance (d) from each atom in a molecule and a set number (n) of reference locations (RLs) in the molecule to obtain a distribution of atomic distances from each reference location (RL) of the molecule for the query molecule and for at least one target molecule ($\vec{M}^t$);

calculating a set number (x) of moments, using the computer, for each obtained distribution of atomic distances from each RL to obtain a set number (y) of shape descriptors for the query molecule and the target molecule; and calculating a similarity score, using the computer, for the query molecule and target molecule from the set of shape descriptors for each molecule, wherein the similarity score indicates the amount of similarity between the query molecule and the at least one target molecule, wherein the similarity score is calculated from the group selected from at least one of the following calculations:
a) the similarity score is calculated by a monotonic inverse function of the distance between the set of shape descriptors for the query molecule and the at least one target molecule; b) the similarity score is calculated by taking an inverse of a translated and scaled Manhattan distance between a vector of shape descriptors from the query molecule ($\vec{M}^q$) and a vector of shape descriptors from the target molecule ($\vec{M}^i$), wherein a similarity score ($S_{qi}$) value of 1 indicates maximum similarity and a value of 0 indicates minimum similarity between the query molecule and the at least one target molecule; or c) the similarity score ($S_{qi}$) is calculated using the following formula:

$$S_{qi} = \left(1 + \frac{1}{12}\sum_{l=1}^{12}\left|\vec{M}^q - \vec{M}^i\right|\right)^{-1}$$

wherein $0 \leq S_{qi} \leq 1$,
and $\vec{M}^q$ and $\vec{M}^i$ are vectors of shape descriptors for the query and $i^{th}$ screened molecule.

7. The method of claim 1, further comprising:
calculating a similarity score for the query molecule and a plurality of target molecules; and
ranking the molecules according to the similarity score.

8. The method of claim 7, wherein the plurality of target molecules are selected from a database of molecules.

9. A computer-implemented method for screening molecules in a database based on shape similarity to a query molecule comprising:
calculating, using the computer, a distance (d) from each atom in a molecule and a set number (n) of reference locations (RLs) to obtain a distribution of atomic distances from each reference location (RL) for the molecule for the query molecule and for molecules selected from the database to be searched;
calculating a set number (x) of moments, using the computer, for each obtained distribution of atomic distances from each RL to obtain a set number (y) of shape descriptors for the query molecule and for each molecule selected from the database;
calculating a similarity score, using the computer, for the query molecule and each molecule selected from the database from the set of shape descriptors for each molecule, wherein the similarity score indicates the amount of similarity between the query molecule (q) and a given molecule (i) selected from the database; and
ranking the molecules, using the computer, selected from the database according to their similarity scores, wherein n is at least 3.

10. The method of claim 9, wherein n is at least 4 and wherein the reference locations comprise at least the following reference locations: the molecular centroid (ctd), the closest atom to ctd (cst), the farthest atom from ctd (fct), and the farthest atom from fct (ftf).

11. The method of claim 9 wherein x is at least 3.

12. A computer-implemented method for screening molecules in a database based on shape similarity to a query molecule comprising:
Calculating a distance (d) from each atom in a molecule and a set number (n) of reference locations (RLs), using the computer, to obtain a distribution of atomic distances from each reference location (RL) for the molecule for the query molecule and for molecules selected from the database to be searched;
calculating a set number (x) of moments, using the computer, for each obtained distribution of atomic distances from each RL to obtain a set number (y) of shape descriptors for the query molecule and for each molecule selected from the database;
calculating a similarity score, using the computer, for the query molecule and each molecule selected from the database from the set of shape descriptors for each molecule, wherein the similarity score indicates the amount of similarity between the query molecule (q) and a given molecule (i) selected from the database; and
ranking the molecules, using the computer, selected from the database according to their similarity scores,
wherein the moments are selected from at least the first three moments of the distribution of atomic distances from the reference location, wherein the first moment is the mean atomic distance to the reference location, the second moment is the variance of the atomic distances from the reference location, and the third moment is skewness of the atomic distances about the reference location.

13. The method of claim 9, wherein n is 4 and x is 3, resulting in 12 shape descriptors for calculation of the similarity score.

14. A computer-implemented method for screening molecules in a database based on shape similarity to a query molecule comprising:
calculating, using the computer, a distance (d) from each atom in a molecule and a set number (n) of reference locations (RLs) to obtain a distribution of atomic distances from each reference location (RL) for the molecule for the query molecule and for molecules selected from the database to be searched;
calculating a set number (x) of moments, using the computer, for each obtained distribution of atomic distances from each RL to obtain a set number (y) of shape descriptors for the query molecule and for each molecule selected from the database;
calculating a similarity score, using the computer, for the query molecule and each molecule selected from the database from the set of shape descriptors for each molecule, wherein the similarity score indicates the amount of similarity between the query molecule (q) and a given molecule (i) selected from the database; and
ranking the molecules, using the computer, selected from the database according to their similarity scores, wherein the similarity score is calculated from the group selected from at least one of the following calculations:
a) the similarity score is calculated by a monotonic inverse function of the distance between the set of shape descriptors for the query molecule (q) and a given molecule (i) selected from the database; b) the similarity score is calculated by taking an inverse of a translated and scaled Manhattan distance between a vector of shape descriptors from the query molecule (q) and a vector of shape descriptors from the given target molecule (i), wherein a similarity score ($S_{qi}$) value of 1 indicates maximum similarity and a value of 0 indicates minimum similarity between the query molecule (q) and a given molecule (i) selected from the database; or c) the similarity score ($S_{qi}$) is calculated using the following formula:

$$S_{qi} = \left(1 + \frac{1}{12}\sum_{l=1}^{12}\left|\vec{M}^q - \vec{M}^i\right|\right)^{-1},$$

wherein $0 \leq S_{qi} \leq 1$, and $\vec{M}^q$ and $\vec{M}^i$ are vectors of shape descriptors for the query and $i^{th}$ screened target molecule.

15. The method of claim 1, wherein the step of calculating a distance (d) from each atom in the molecule involves first, using the computer, reading a three-dimensional position vector for each atom in the molecule, determining using the computer the location of each RL of the molecule to be used from the positions of the atoms in the molecule, and then using the computer calculating a set of Euclidean distances of all atoms to at least one RL.

16. The method of claim 9, wherein the step of calculating a distance (d) from each atom in the molecule involves first, using the computer, reading a three-dimensional position vector for each atom in the molecule, determining using the computer the location of each RL of the molecule to be used from the atomic positions of the atoms in the molecule, and then using the computer calculating a set of Euclidean distances of all atoms to at least one RL.

17. The method of claim 4, wherein the first moment provides an average atomic to the molecular centroid, the second moment provides a variance of the atomic distances about the first moment and the third moment provides a skewness of the atomic distances about the first moment.

18. The method of claim 9, wherein the first moment provides an average atomic to the molecular centroid, the second moment provides a variance of the atomic distances about the first moment and the third moment provides a skewness of the atomic distances about the first moment.

* * * * *